US00PP19368P2

(12) United States Plant Patent
White

(10) Patent No.: US PP19,368 P2
(45) Date of Patent: Oct. 21, 2008

(54) MINIATURE ROSE PLANT NAMED 'SAVALODE'

(50) Latin Name: ***Rosa hybrida* 'minima'**
Varietal Denomination: SAValode

(75) Inventor: Wendy White, Ipswich, MA (US)

(73) Assignee: Nor'East Miniature Roses, Arroyo Grande, CA (US)

( * ) Notice: Subject to any disclaimer, the term of this patent is extended or adjusted under 35 U.S.C. 154(b) by 0 days.

(21) Appl. No.: 11/895,530

(22) Filed: Aug. 24, 2007

(51) Int. Cl.
*A01H 5/00* (2006.01)

(52) U.S. Cl. ..... Plt./119
(58) Field of Classification Search ..... Plt./119, Plt./118, 125, 126
See application file for complete search history.

*Primary Examiner*—Kent L. Bell
*Assistant Examiner*—June Hwu

(57) ABSTRACT

'SAValode' is a new and distinct variety of miniature rose plant noted for its golden-yellow flowers, borne continuously through the growing season. The plant is clean, extremely vigorous and well branched, remaining mounded and compact.

1 Drawing Sheet

Genus and species: *Rosa hybrida* 'minima'.
Varietal denomination: 'SAValode'

CROSS REFERENCE

Three roses in this same breeding program can be compared with this new invention: 'SAVabusy' (U.S. Plant patent application Ser. No. 10/021,857, filed Dec. 17, 2003 — abandoned) and 'SAVapple' (U.S. Plant Pat. No. 13,055, and 'SAVadiana', (U.S. Plant Pat. No. 16,797). These plants all have very good vigor; a compact, well-branched, mounding plant habit; and continuous blooming habits. While all these plants primarily have 5-leaflet leaves, they also occasionally have 7-leaflet leaves. 'SAVabusy' and this new invention also have the same plant size of 14-inches tall and mounded to 24-inches wide. The most notable differences are in the color of the flowers. 'SAVabusy' has flowers in shades of orange-red. 'SAVapple' has coral colored flowers. 'SAVadiana' has deep lemon-yellow flowers. This new invention has golden-yellow flowers. The parentages of 'SAVabusy', 'SAVapple' and 'SAVadiana' can be traced back two generations and this new invention to the third generation to show they are related through 'MEIgronuri' (U.S. Plant Pat. No. 4,625).

BACKGROUND OF THE INVENTION

This present invention relates to a new and distinct variety of hardy, bush type plant of the miniature class. This variety was created by myself, Wendy R. White, under controlled conditions in a greenhouse in Rowley, Mass., by crossing, as seed parent, the variety known as 'SAVibunda' (U.S. Pat. No. 18,796 with an unnamed and unintroduced deep pink seedling, of 'SAVasach' (U.S. Plant Pat. No. 5,967) by 'LAVjune' (U.S. Plant Pat. No. 6,859), from this same breeding program, as pollen parent.

The idyllic goals of the breeding program were to create unique miniature roses with as many of the qualities as possible of vigor, disease resistance, hardiness, exhibition, hybrid tea-form blooms born in abundance from late spring to late fall, and fragrance. The cultivar chosen as seed parent is known for its well above average disease resistance, abundance of bloom, hardiness and vigor. The seedling chosen as pollen parent was known for its above average disease resistance, its winter hardiness, being first to bloom in the spring, its abundance of bloom, its vigor, its strong fragrance and its miniature size. This resulting new cultivar has very good vigor, abundant bloom production throughout the growing season, good disease resistance, and uniquely colored flowers having moderate fragrance. This resulting new cultivar has been named 'SAValode'.

Asexual reproduction by cuttings of this new cultivar in Rowley, Mass. and Arroyo Grande, Calif. shows that all distinguishing characteristics of this new rose continually come true to form.

BRIEF SUMMARY OF THE INVENTION

This present invention relates to a new, distinct and low growing variety of hardy, bush type, miniature rose plant that is primarily characterized by its semi-double, golden-yellow blooms borne in abundance throughout the growing season.

It is easily distinguished from its parent. Its seen parent, 'SAVibunda', is a very light yellow floribunda, with flowers and a plant habit much larger than this new introduction. Its pollen parent was a miniature rose but slightly larger, growing to 15 to 18 inches tall and wide compared to only 14 inches tall but 24 inches wide of this new cultivar, and having deep pink double flowers that measured around 2½-inches in diameter when full open compared to golden-yellow flowers of around 1¾-inches full open on the new cultivar.

The characteristics most distinguishing this new invention from its parents and all other varieties of which I am aware are its truly golden-yellow, miniature flowers on a vigorous, low-growing and very well branched miniature plant. The variety is further characterized by:

- rapid repeat bloom cycle on young plants to continuous bloom production on mature plants from late spring to mid-fall;
- little fade as the flower ages;

- flowers that open fully to expose filaments that match the color of the petals and small stamens of a dark yellow-orange;
- its mild fragrance;
- few to no prickles on young growth;
- the dark color of the foliage;
- its vigorous growth and abundant bloom production both in the greenhouse and outdoors, providing decoration in containers or in the ground as a perennial.

BRIEF DESCRIPTION OF THE DRAWING

In the accompanying drawing, the upper image shows buds, flowers and foliage of this new invention as grown in Arroyo Grande, Calif. in July in greenhouses with roofs that open on sunny days exposing the plants to direct sunlight. Those plants were on a regulated feeding program.

The lower image is of a young stem with thorns and a developing hip shown at actual size, on a one-year-old plant that had been growing in the ground for 5 weeks in August in Essex County, Mass. This plant received no supplemental feeding after it was planted in the ground to enable the development of the hips.

BOTANICAL DESCRIPTION OF THE PLANT

The following observations, measurements, and values describe one year old plants of *Rosa hybrida minima,* 'SAValode', of the miniature rose class, grown in 3½-inch plastic containers in a soilless mix of peat moss and ground coconut bark. These plants spent their first 7 months or so growing in plastic covered greenhouses in Arroyo Grande, Calif. They finished with those pots being kept outside in Essex County, Mass. Color references are made using The Royal Horticultural Society Colour Chart, except were common terms of color are used. Phenotypic expression will vary with environmental, cultural and climatic conditions, as well as differences in conditions of light and soil.

Parentage: 'SAVibunda' as the seed parent by an unnamed, unintroduced, deep pink seedling of 'SAVasach' by 'LAVjun' as the pollen parent.

FLOWERS

BLOOMING HABIT is rapid repeat to continuous on nature plants throughout the growing season. On mature plants, flowers are borne mostly in small clusters of two or three for the first flush of bloom in the spring. The remainder of the season, flowers are borne both singly and in small clusters.

BUD form is narrow-ovate with an acute apex and a rounded base. The length of the bud varies from 9/16- to 11/16-inch and width varies from 5/16- to 6/16-inch.

SEPALS: The flower has five sepals. The color of the outer surfaces is a medium- to dark-green, near 137C with the basal area and going up into the center of the sepal being a yellow-green, between 146A and 146B, and extensions of near 137B.

All sepals of the full open flower are about ¼-inch wide. The two outermost sepals are 12/16- 13/16-inch long. Their form is lanceolate with lanceolate apices. The remaining three sepals are about 11/16-inch long and are ovate-lanceolate with acuminate apices.

All sepals have a pubescent inside surfaces of appressed down and ciliated margins. The two outermost sepals also have near evenly spaced stipitate glands along the margins and a single attenuate, foliar appendage along each margin that also has stipitate glands. The outside surfaces of those sepals only have hairs on and just below the apex. The two innermost sepals have appressed hairs covering the entire outer surface and no glands or foliar appendages along the margins. The one sepal in-between the inner and outer sepals displays characteristics of both the inner and outer sepals, with one half of the outer surface having a hairy covering and no foliar appendages or glands along the margins, as on the inner sepals, and the other half having no hairs on its outer surface but with stipitate glands and a single foliar appendage along its margin as is found on the outer sepals.

Sepals roll back with the petals until the flower is full open and then continue rolling back until they are appressed against the peduncle. They remain attached to the receptacle after the petals drop and may slowly being to return to perpendicular to the receptacle. If a hip develops, the sepals again roll back and may remain appressed to the hip while the hip matures.

The RECEPTACLE is funnel shaped with a glabrous and glossy surface. The color is a medium green, near 144A to 144B. The diameter is between 7/32- to 9/32-inch and 9/32-inch in height. The surface on top of the receptacle is glabrous with a diameter ranging from 7/32- to 9/32-inch. The color is a light yellow, near 16D.

PEDUNCLES are straight and very strong. Anthocyanin coloring is absent. The surface is glossy with a darker color than the receptacle, being near 146C. The surface has some fine hairs and stipitate glands. The length of the peduncle varies from ½- to ⅝-inch with a diameter of ⅛-inch. The base of the peduncle is oblique where it attaches to the stem. The lower side usually has a three-leaflet leaf at the point of attachment. The higher side usually has a single tri-loded leaf with a pair of stipules the entire or nearly the entire length of its petiole.

BLOOM size, when fully expanded, may be as small as 1 13/16- to 1 14/16-inches in diameter with a depth measured from the top of the receptacle of about ½- to 9/16-inch, and may be as large as 2¾- inches in diameter with a depth measured from the top of the receptacle of 1- to 1 1/16-inches. The flower may open with a flat to slightly concave upper profile, as seen in the accompanying image, or it may open with a slightly higher center with the upper profile becoming flat as it opens. The lower profile is cupped. As the bloom opens it attains a flattened-convex upper profile and an arched lower profile. The upper profile continues to flatten and the outer petals continue to recurve until they drop from the receptacle after 4 to 6 days.

PETALS are imbricated, regularly overlapping. Petalage may vary from 21 to 28, usually with 0 to 5 petaloids. From the time the sepals first divide until the petals start to unfurl is between 2 and 4 days, with another 2 to 3 day until the petals are fully extended. Petals begin to drop after an additional 2 to 3 days. Fragrance is slight to moderate.

Petals are thin to medium with a satiny upper and lower surface. Outer petals are broad ovate with a rounded margin and notch beside an acute tip at the apex. The inner petals are ovate with just as acute apex. The base of the petals varies from broadly obtuse to deltoid. Outermost petals measure from 21/31- 23/32-inch wide and ¾- to 15/16-inch long.

COLOR of the flowers does vary with the intensity of light and nutrients. Generally the color of the upper petal surface during the first few days is near 29C to 29D, a light peach, the blends in with near 16D, a medium yellow, from the basal area. The blending of these colors gives the appearance of being golden-yellow. The point of attachment is a light yellow, near 3C. The reverse of the petals is also near 29C-D and blends in with Chartreuse Green, near 1D, from the base and at the point of attachment.

There is not much change in color as the flower ages. The upper surface of the petals lightens only a little to near 29D blended in with the near 16D. The point of attachment darkens to near 15C, a Chrome Yellow. The reverse becomes are 24C to 24D, a Tangerine/Apricot, blended with near 16D from the basal area. The point of attachment has darkened to between 20A and 16D. At petal drop the color of all surfaces is near 26C, a Spanish Orange, blended in with near 16D and all basal areas are near 16D.

PETALOIDS, when present, have the same coloring as the petals. Their width varies from 1/8- to 1/2-inch with a length of 1/2- to 3/4-inch. The wider petaloids are usually deeply cleft. All margins are curved inward and misshapen.

General tonality of the flowers is always a golden-yellow. From a distance these flowers appear golden-yellow.

REPRODUCTIVE ORGANS

Androecium: STAMENS are arranged regularly around the outer edge of the receptacle, adjacent to the petals. They range in quantity from 75 to 108. The anthers are near the same color as the basal area of the petals, 16B to 16C. The pollen sacs are near 22C, an Orange Buff, but quickly age to a deeper orange, between 22A and 163A. Pollen is virile. The length of the filaments varies from 1/8- to 1/4-inch for those nearest the center of the flower with longer filaments, from 3/32- to 3/8-inch, adjacent to the petals. They tend to be recurved, which increases as the flower matures. Their color is between 15D and 17D.

PISTILS are one-fourth to one-third the quantity of stamens. Styles are generally straight but deltoid, with a top width of near 1/64 inch and tapering down from there. They are about 3/32-inch long with 2/32-inch above the receptacle surface and 1/32-inch below the surface, in an alveola at the center of the top of the receptacle. The color near the top is red, near 53D, and at the base is a light color from the Greyed-Orange Group, near 164D. The Stigmas are lighter than this, near 161D.

There are not mature hips to observe at this time. The shape of the maturing hip is conical to urceolate. The largest hip currently measures 11/16-inch in diameter and height. The surface exposed to the sun is becoming flushed with near 183A, indicating the hips may have reached their mature size. Where the sepals are protecting the surface from the sun, it remains a medium green, between 144A and 146B. The surface is glabrous.

PLANT

The plant has excellent vigor and is heavily and uniformly branched. The plant generally grows to 14-inch tall and spreads to 24-inches wide. Flowering stems vary from 2 1/4- to 3-inches long.

FOLIAGE is pinnately compound, generally with 5 leaflets but may have 7 or 3. There are usually four leaves on the flowering stems, regardless of the length of the stem. The length of the mature leaves on the young plants used for this evaluation varied from 2 3/4- to 3 1/4-inches long from tip of the terminal leaflet to attachment to stem, when measured along the rachis. Mature terminal leaflets measured 11/16—15/16-inch at the widest point and 1 3/16 to 1 6/16-inches long.

Leaflets have a semi-glossy and glabrous upper surface. The undersurface is matte and leathery with the central vein protruding and the lateral veins recessed slightly. Margins have a simple and near each serration with each serrate tipped with a gland.

COLOR of the foliage is generally a very dark green. Old foliage is between 139A and 137A. The surface is lighter, between 137C and 147B. New foliage is lighter and a bit more yellow-green than the old foliage, between 137B to 137C to 146B to 146C, and may be flushed, especially along the margins, with near 183A. The under surface is between 144B and 146C, with the entire surface slightly flushed with near 184A to 184B, darkest along the margins.

PETIOLES and RACHIS and PETIOLULES are similar. On mature leaves their color is a medium to dark yellow-green, near 146B and flushed lightly with near 178A from the Greyed-Red Group. Ridges are flushed a bit heavier and are lined with near evenly spaced stipitate glands. The underside is a deeper green between 137A and 147B. The petiole was measured about 15/32-inch long and the underside is glossy and glabrous. The rachis was measured at 15/16-inch long, with a glossy underside and may have no to 3 prickles of varying lengths. The underside of the petiolule to the terminal leaflet may have a single prickle. Length of the petiolules to the terminal leaflet varies between 13/32- to 1/2-inch and to the other leaflets it has a length of 2/32 to 3/32-inch.

Stipules are attached along each side of the petioles with an average 5/16-inch attached to the petiole and an additional 5/32-inch angled out at about a 45-degree angle from the petiole. These lengths can vary by 1/64-inch, more or less. The color is a medium yellow-green, near 146C, in the groove and near 146A to 146B along the ridges. The area closest to the petiole usually has some flushing along the ridges. The reverse of the stipules is the same color as the reverse of the petiole to which they are attached, between 137A and 147B. Margins are recurved and edged with stipitate glands.

WOOD: New growth is medium yellow-green, near 144B. The sunward side may be flushed with near 184C. Color of the older canes is darker green, between 146A and 137B. Main stalks are 5/16-inch in diameter. Diameters of primary laterals are about 3/16-inch and of secondary laterals are 2/16- and 3/32-inch. The texture of the new wood is glabrous and the color is between 137C and 146A. Lenticels may start forming on the main canes and primary laterals in the first year of growth. Where lenticels have appeared their color begins as between 174B and 177B to 177C and darkens to near 177A, a dark brown from the Greyed-Orange Group.

The longest prickles observed were 7/32-inch long attached to a base that was 6/32-inch long. Their shape is acuminate. Prickles on young growth appear translucent and near 180C. Color on older prickles is near 178A to 178B. There may also be random smaller prickles of about 1/8-inch long scattered between these longer prickles. Quantity and spacing appear to be erractic, with some canes having no prickles to a few canes having some of the longer prickles and many shorter prickles.

This new cultivar has been tested hardy in USDA zones 5 through 10. Resistance to blackspot, rust, and downy and powdery mildews was found to be good.

What is claimed is:

1. A claim a new and distinct variety of hardy rose plant of the miniature class, substantially as illustrated and described, characterized particularly as to novelty by the distinctive golden-yellow color of its blooms and the exceptional vigor of the plant, and being suitable for production from softwood cuttings in pots.

* * * * *

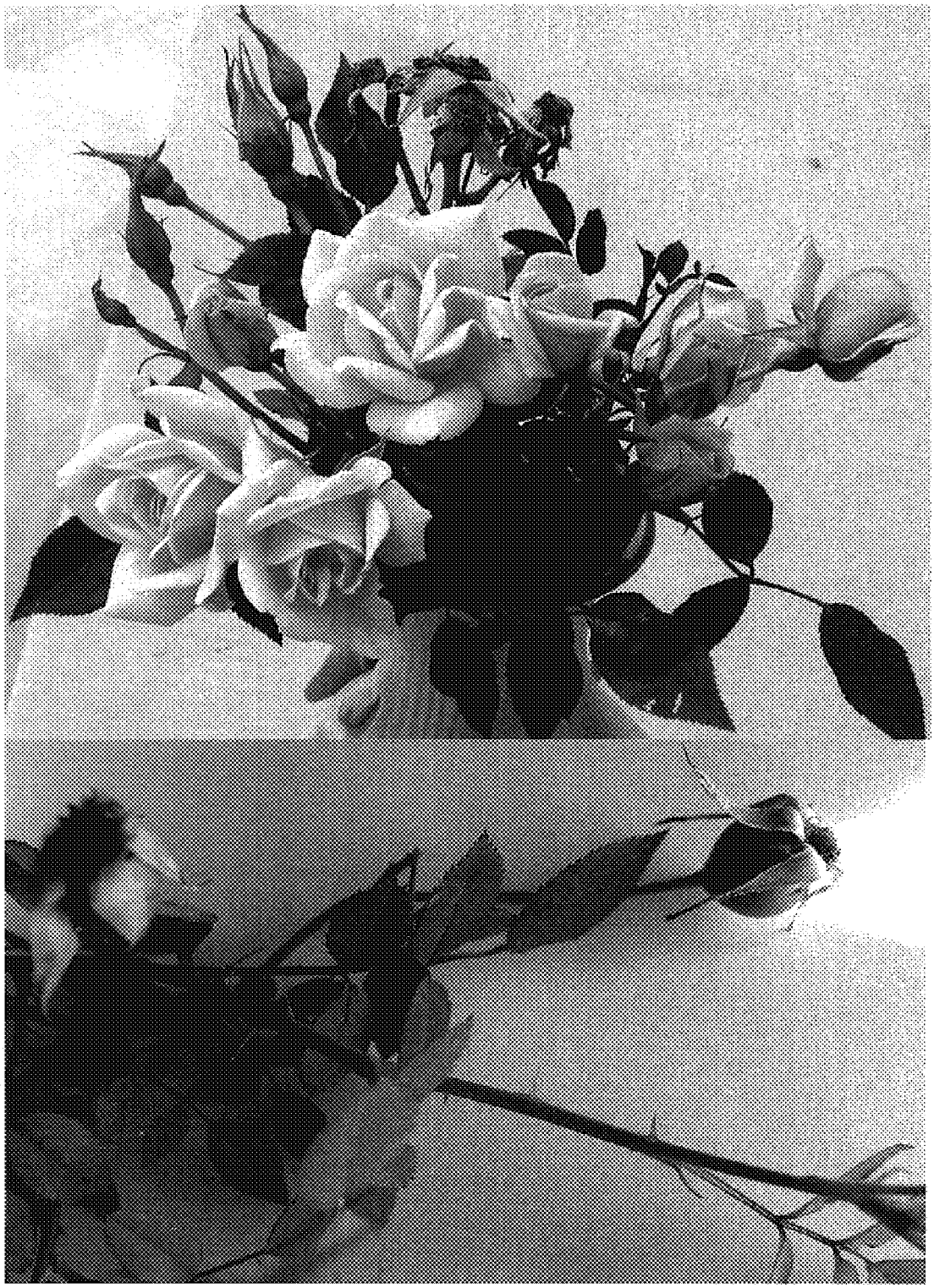

UNITED STATES PATENT AND TRADEMARK OFFICE

CERTIFICATE OF CORRECTION

PATENT NO. : PP 19,368 P2
APPLICATION NO. : 11/895530
DATED : October 21, 2008
INVENTOR(S) : Wendy White It is certified that error appears in the above-identified patent and that said Letters Patent is hereby corrected as shown below:

Column 1, close parentheses were omitted in two instances. At the end of the 4th line after CROSS REFERENCE: "(U.S. Plant Pat. No. 13,055, and" should read --(U.S. Plant Pat. No. 13,055), and--; the beginning of the 11th line from the bottom: "No. 18,796 with an unnamed" should read --No. 18,796) with an unnamed--

Column 2, the end of Line 21: "Its seen parent," should read --Its seed parents,--

Column 4, the beginning of the 8th line from the bottom: "ovate with just as acute apex." should read --ovate with just an acute apex.--; the beginning of the 2nd line from the bottom: "peach, the blends in with" should read --peach, that blends in with--

Column 5, at the end of Line 8: "The reverse becomes are" should read --The reverse becomes near--; at the end of the 15th line from the bottom: "grows to 14-inch tall and" should read --grows to 14-inches tall and--

Column 6, the beginning of Line 1: "have a simple and near each serration" should read --have a simple and near even serration--; the first line of the claim, which is the 6th line from the bottom: "1. A claim a new and distinct" should read --1. I claim a new and distinct--

Signed and Sealed this

Twenty-fourth Day of March, 2009

John Doll

JOHN DOLL
*Acting Director of the United States Patent and Trademark Office*